United States Patent [19]

VandenBerg

[11] Patent Number: Plant 7,482

[45] Date of Patent: Mar. 26, 1991

[54] CHRYSANTHEMUM PLANT NAMED TAYRONA

[75] Inventor: Cornelis P. VandenBerg, Salinas, Calif.

[73] Assignee: Yoder Brothers, Inc., Barberton, Ohio

[21] Appl. No.: 481,069

[22] Filed: Feb. 16, 1990

[51] Int. Cl.[5] ..... A01H 5/00

[52] U.S. Cl. ..... Plt./77

[58] Field of Search ..... Plt./77

*Primary Examiner*—Howard J. Locker

*Attorney, Agent, or Firm*—Foley & Lardner, Schwartz, Jeffery, Schwaab, Mack, Blumenthal & Evans

[57] ABSTRACT

A Chrysanthemum plant named Tayrona particularly characterized by its flat capitulum form; decorative capitulum type; white ray floret color, with a fresh green center of the flower; diameter across face of capitulum of 63 to 73 mm when fully opened; photoperiodic flowering response to short days of 50 to 52 days when grown in Salinas, Calif., and 64 to 67 days when grown in Bogota, Colombia; peduncle length of the first lateral of 13 to 18 cm, and of the fourth lateral of 18 to 23 cm, when grown without growth regulator applications, on open, terminal sprays; plant height of 76 to 86 cm when grown as a single stem spray cut mum in Salinas, Calif. with 6 to 8 long days prior to start of short days compared to a height of 97 to 117 cm when grown in Bogota, Colombia with 14 to 15 long days prior to start of short days; and excellent tolerance to low night temperatures for bud initiation and flower development.

3 Drawing Sheets

The present invention comprises a new and distinct cultivar of Chrysanthemum, botanically known as *Dendranthema grandiflora,* and referred to by the cultivar name Tayrona.

Tayrona, identified as 85-249004, was originated from a cross made by Cornelis P. VandenBerg in a controlled breeding program in Salinas, Calif., in 1984.

The female parent of Tayrona was an unnamed seedling identified as 81-651001, and described as a yellow decorative cut spray mum. The male parent of Tayrona was also an unnamed seedling, identified as 82-J38047, and described as a white decorative cut spray mum with a high number of disc florets.

Tayrona was discovered and selected as one flowering plant within the progeny of the stated cross by Cornelis P. VandenBerg in March 1986, in a controlled environment in Salinas, Calif.

The first act of asexual reproduction of Tayrona was accomplished when vegetative cuttings were taken from the initial selection in May 1986 in a controlled environment in Salinas, Calif., by technicians working under the supervision of Cornelis P. VandenBerg.

Horticultural examination of controlled flowerings of successive plantings has shown that the unique combination of characteristics as herein disclosed for Tayrona are firmly fixed and are retained through successive generations of asexual reproduction.

Tayrona has not been observed under all possible environmental conditions. The phenotype may vary significantly with variations in environment such as temperature, light intensity and daylength. For example, plant height will increase with an increased number of long days after planting prior to start of short days. Under low night temperature (10 degrees Celsius and lower) flowering can be expected to be delayed. Under high temperatures (25 degrees Celsius night and 35 degrees Celsius day) flowering can be expected to be delayed and be more uneven than under normal temperatures. Normal temperatures can be described as 15 degrees Celsius minimum night and 25 degrees Celsius maximum day.

The following observations, measurements and comparisons describe plants grown in Salinas, Calif. and in Bogota, Colombia, under greenhouse conditions which approximate those generally used in commercial greenhouse practice. The low temperature tolerance was determined in repeated flowerings in Bogota, Colombia.

The following traits have been repeatedly observed and are determined to be basic characteristics of Tayrona, which, in combination, distinguish this Chrysanthemum as a new and distinct cultivar:

1. Flat capitulum form.
2. Decorative capitulum type.
3. White ray floret color, with a fresh green center of the flower.
4. Diameter across face of capitulum of 63 to 73 mm when fully opened.
5. Flowering response in Salinas under normal temperatures is 50 to 52 days after start of short days. Flowering response in Bogota, Colombia under temperatures of minimum 7 degrees Celsius night and maximum 29 degrees Celsius day is 64 to 67 days after start of short days.
6. Peduncle length of the first lateral at flowering after removing the apical bud without growth regulator applications is 13 to 18 cm when grown in Salinas, Calif., and 13 to 15 cm when grown in Bogota, Colombia. Peduncle length of the fourth lateral at flowering is 20 to 23 cm when grown in Salinas, and 18 to 23 cm when grown in Bogota.
7. Plant height is 76 to 86 cm when grown in Salinas with 6 to 8 long days prior to start of short days; height is 97 to 117 cm when grown in Bogota with 14 to 15 long days prior to start of short days.
8. Excellent tolerance to low night temperatures for bud initiation and flower development. Average minimum low night temperatures in our Bogota trials ranged from 7 to 8.5 degrees Celsius.

The above measurements represent repeated flowerings over a period of a minimum of two years.

The accompanying photographic drawings show typical inflorescence and leaf characteristics of Tayrona, with the colors being as nearly true as possible with illustrations of this type.

Sheet 1 is a color photograph of Tayrona grown as a single stem cut spray mum.

Sheet 2 is a black and white photograph of three views of the inflorescence of Tayrona.

Sheet 3 is a black and white photograph showing the upper and under sides of the leaves of Tayrona at three stages of development (mature, intermediate and immature).

Of the commercial cultivars known to the inventor, the most similar in comparison to Tayrona is the unpatented cultivar Polaris, a white decorative spray cut mum. Reference is made to attached Chart A, which compares certain characteristics of Tayrona to the same characteristics of Polaris.

Similar traits are capitulum form and type, spray formation, and low night temperature tolerance. Flowering response of Tayrona has been very similar to the response of Polaris in Salinas trials, but has been 5 to 6 days faster than the response to Polaris in Bogota trials. Tayrona has a clear white flower color with a fresh green center of the flower, compared to a creamy white flower color of Polaris. Tayrona also has a smaller flower, and a shorter plant height than Polaris. The peduncle length of both cultivars is comparable.

In the following description color references are made to The Royal Horticultural Society Colour Chart. The clear white ray floret color of Tayrona is not represented in the RHS color chart. The color values were determined on plant material grown in Salinas, Calif. on July 17, 1989.

Classification:

*Botanical.*—*Dendranthema grandiflora* cv Tayrona.

*Commercial.*—Decorative cut spray mum.

INFLORESCENCE

A. Capitulum:

*Form.*—Flat.

*Type.*—Decorative.

*Diameter across face.*—63 to 73 mm when fully opened.

B. Corolla of ray florets:

*Color (general tonality from a distance of three meters).*—Clear white, with green center of flower.

*Color (upper surface).*—Clear white, towards center of flower 150D to 150C. Mid-center overcast with 144A.

*Color (under surface).*—Clear white.

*Shape.*—Outer petals straight, inner petals slightly incurved; cross section concave.

C. Corolla of disc florets:

*Color (mature).*—Closest to 14A.

*Color (immature).*—Closest to 144A.

D. Reproductive organs:

*Androecium.*—Present on disc florets only; few disc florets; scant pollen.

*Gynoecium.*—Present on both ray and disc florets.

PLANT

A. General appearance:

*Height.*—76 to 86 cm when grown as a single stem cut mum with 6 to 8 long days prior to start of short days in Salinas, Calif.; 97 to 117 cm when grown with 14 to 15 long days prior to start of short days in Bogota, Colombia.

B. Foliage:

*Color (upper surface).*—147A.

*Color (under surface).*—147B.

*Shape.*—See photograph.

CHART A

COMPARISON OF TAYRONA AND POLARIS

| CHARACTERISTIC | TAYRONA | POLARIS |
|---|---|---|
| Ray floret color | Clear white, with fresh green center of flower | Creamy white |
| Capitulum form | Flat | Flat |
| Capitulum type | Decorative | Decorative |
| Spray formation | Terminal | Terminal |
| Peduncle length: | | |
| 1st lateral, Salinas | 13 to 18 cm | 14 to 15 cm |
| 4th lateral, Salinas | 20 to 23 cm | 18 to 20 cm |
| 1st lateral, Bogota | 15 to 18 cm | 15 to 18 cm |
| 4th lateral, Bogota | 18 to 23 cm | 20 to 23 cm |
| Diameter across face of capitulum | 63 to 73 mm | 76 to 83 mm |
| Plant height: | | |
| 6–8 long days Salinas | 76 to 86 cm | 94 to 104 cm |
| 14–15 long days Bogota | 97 to 117 cm | 107 to 127 cm |
| Flowering response period | | |
| in Salinas | 50 to 52 days | 51 to 53 days |
| in Bogota | 64 to 67 days | 69 to 73 days |
| Low night temperature tolerance | Excellent | Excellent |

COMPARISONS MADE OF PLANTS GROWN AS SINGLE STEM SPRAY CUT MUMS IN SALINAS, CALIFORNIA, AND IN BOGOTA, COLOMBIA

I claim:

1. A new and distinct Chrysanthemum plant named Tayrona, as described and illustrated.

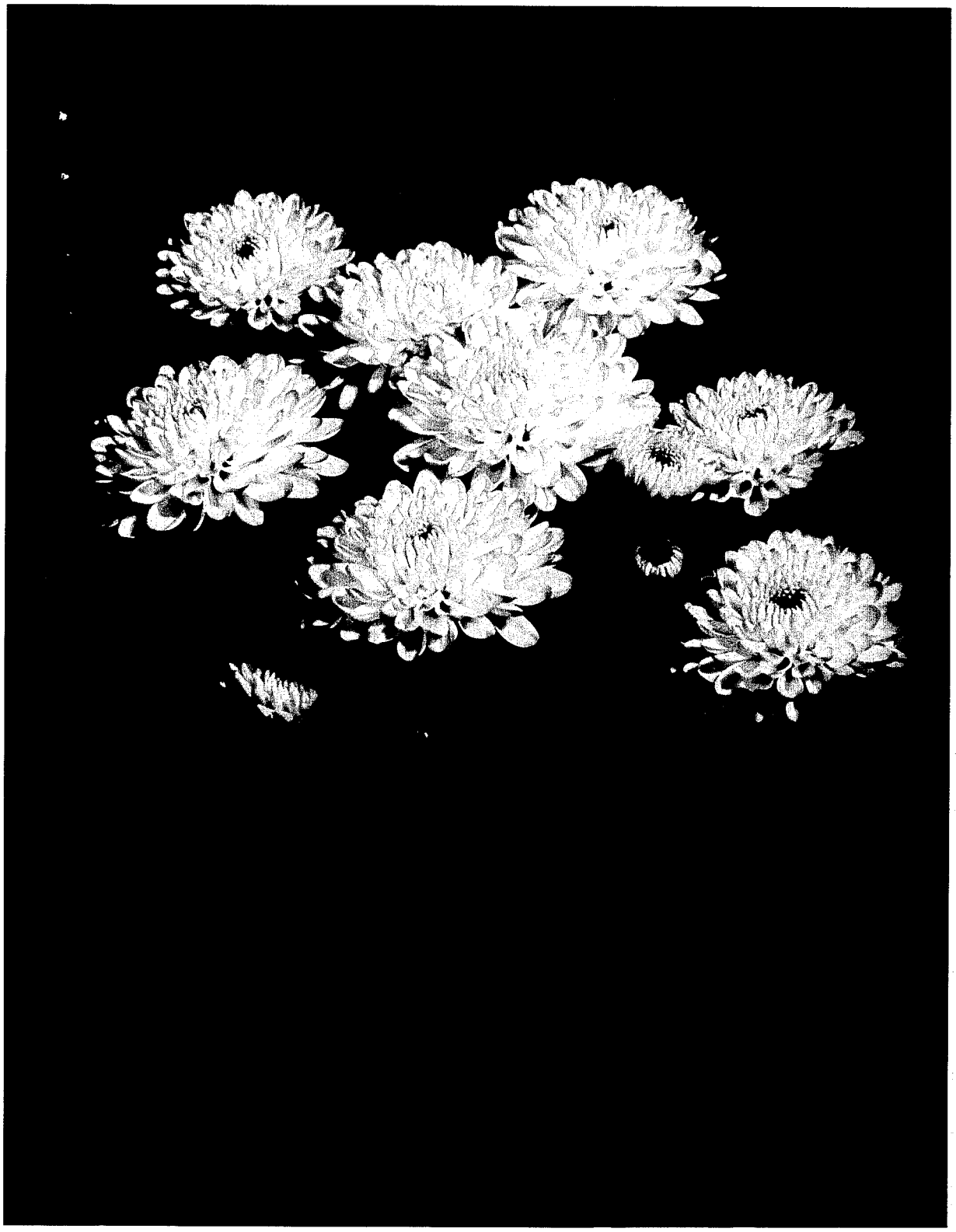

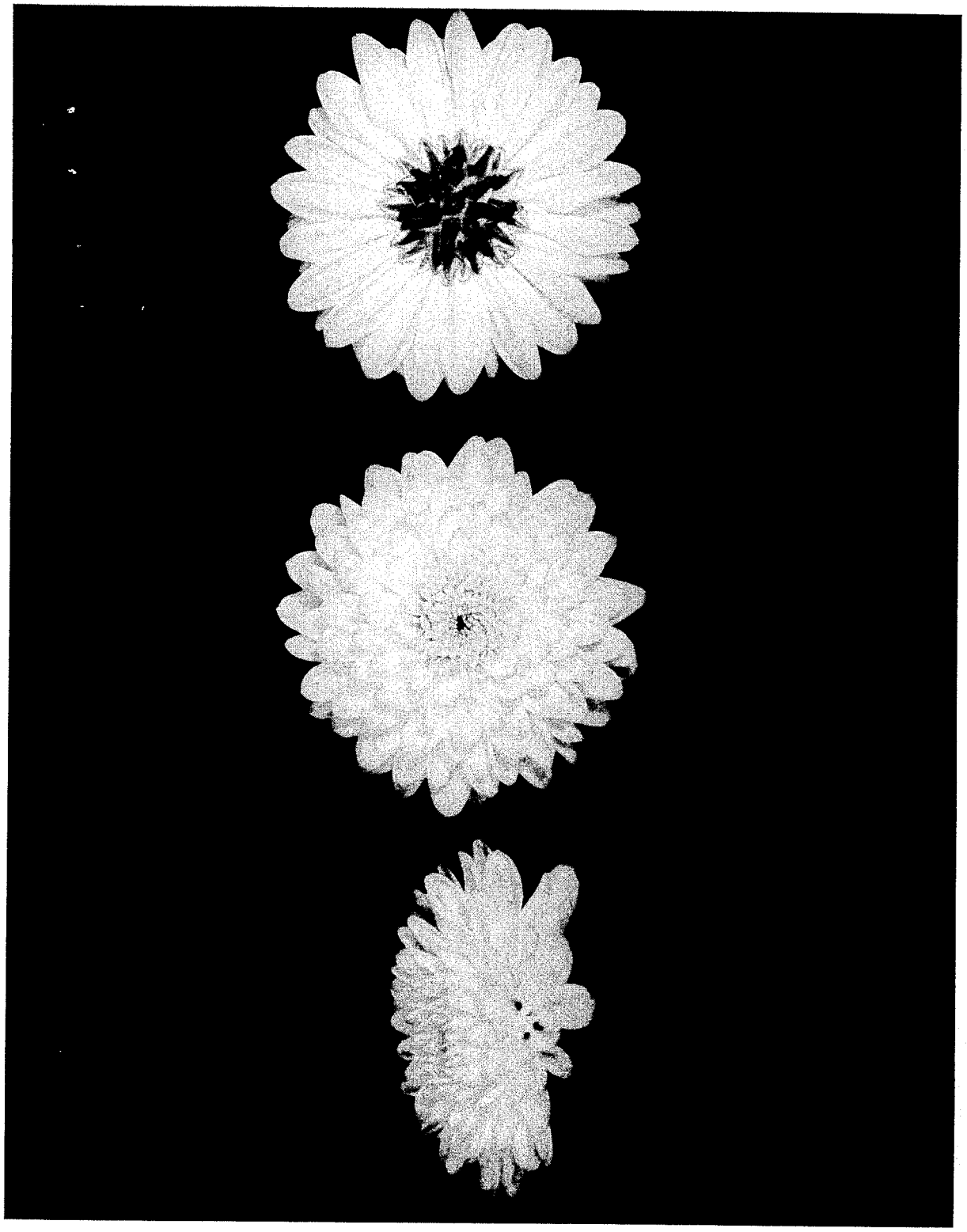

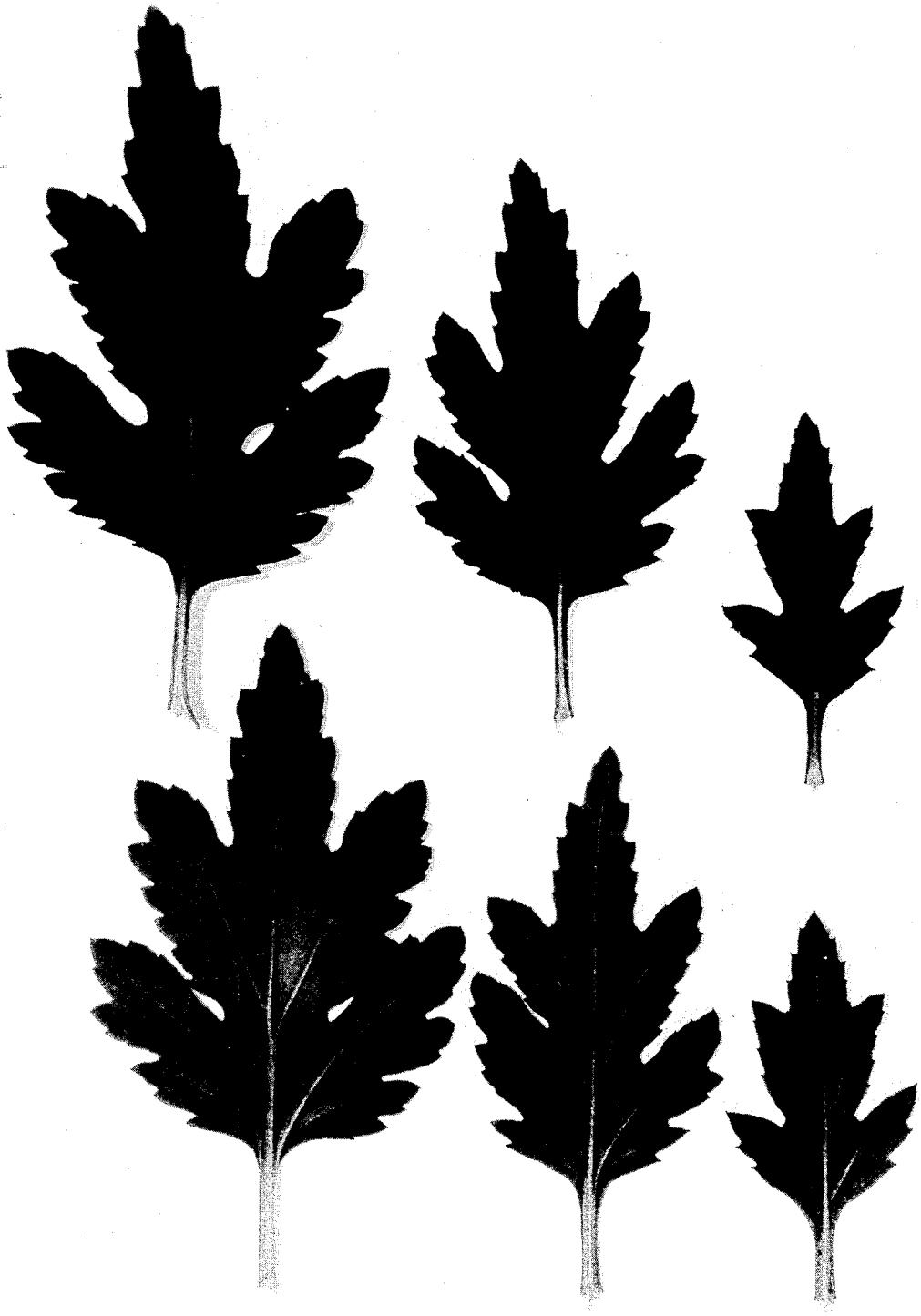

* * * * *